United States Patent
Makino et al.

(10) Patent No.: US 6,864,055 B2
(45) Date of Patent: Mar. 8, 2005

(54) METHOD FOR DETECTING NUCLEIC ACIDS

(75) Inventors: Yoshihiko Makino, Saitama (JP); Yoshihiko Abe, Saitama (JP); Masashi Ogawa, Tokyo (JP); Makoto Takagi, Fukuoka (JP); Shigeori Takenaka, Fukuoka (JP); Kenichi Yamashita, Fukuoka (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/887,625

(22) Filed: Jun. 22, 2001

(65) Prior Publication Data

US 2002/0076717 A1 Jun. 20, 2002

(30) Foreign Application Priority Data

Jun. 22, 2000 (JP) ........................................ 2000-187486

(51) Int. Cl.[7] ........................... C12Q 1/68; C12P 19/34; B01D 57/02; G01N 30/02
(52) U.S. Cl. .......................... 435/6; 435/91.1; 204/452; 204/409; 204/603; 210/656; 422/70
(58) Field of Search .............................. 204/452, 409, 204/603; 210/656; 422/70; 435/6, 91.1

(56) References Cited

U.S. PATENT DOCUMENTS 6,361,671 B1 * 3/2002 Mathies et al.
6,541,617 B1 * 4/2003 Bamdad et al. ............ 536/23.1

* cited by examiner

Primary Examiner—Jezia Riley
(74) Attorney, Agent, or Firm—Reed Smith LLP

(57) ABSTRACT

A method of detecting nucleic acid fragments in plural samples is performed by the steps of: attaching an electroconductive label to nucleic acid fragments in one sample and attaching a different electroconductive label to nucleic acid fragments in another sample; preparing a mixture of these samples; spotting the mixture on an electroconductive microarray having plural electrodes onto which probe molecules complementary to the nucleic acid fragments are fixed, so that hybridization between the nucleic acid fragments and the probe molecules on the electroconductive microarray can proceed to form hybrid structures; applying to the electrode an electric potential corresponding to the oxidation-reduction potential of the former label and detecting on the electrode an electric current; applying to the electrode an electric potential corresponding to the oxidation-reduction potential of the latter label and detecting on the electrode an electric current; and comparing the electric current detected in the former detecting procedure and that detected in the latter detecting procedure.

8 Claims, 3 Drawing Sheets

METHOD FOR DETECTING NUCLEIC ACIDS

CROSS-REFERENCES TO RELATED APPLICATIONS

This application claims priority of Japanese Application No. 2000-187486 filed Jun. 22, 2000, the complete disclosure of which is hereby incorporated by reference.

FIELD OF THE INVENTION

This invention relates to a method for detecting nucleic acid fragments in plural samples. In particular, the invention relates to detection of nucleic acid fragments in plural samples using an electroconductive microarray having probe molecules and utilizing differential hybridization between the nucleic acid fragments and the probe molecules.

BACKGROUND OF THE INVENTION

The gene analysis is recently paid an attention in developing gene technology.

For the gene analysis, microarray is now widely employed. The microarray has a number of areas in each of which probe molecules such as nucleic acid fragments are placed. Sample DNA fragments obtained directly or via PCR technique from the target genes are labeled with fluorescent label and then brought into contact with the probe molecules on the microarrays. When the sample DNA fragments are complementary to the probe molecules on the microarray, hybridization occurs so that the sample DNA fragments are combined with the probe molecules, to form hybrid structures on the microarray. Thus formed hybrid structures can be locating by detecting the fluorescent label of the combined target DNA fragments.

The microarray is particularly useful for the purpose of gene expression analysis.

For instance, Patrick O. Brown & David Botstein describe in "Exploring the new world of the genome with DNP microarrays" (Nature Genetics Supplement, Vol. 21, January 1999, pp. 33–37), differential hybridization using different fluorescent labels. In the differential hybridization procedure, one of different fluorescent labels is attached to DNA fragments in one sample, while another fluorescent label is attached to DNA fragments in another sample. Both samples are spotted on a microarray for performing hybridization to form hybrid structures. The positions of thus formed hybrid structures are located by detecting each of fluorescent labels of the hybrid structures on the microarray. The detected data are compared with each other to analyze difference between DNA composition of one sample and DNA composition of another sample.

U.S. Pat. No. 5,800,992 describes a method for detecting nucleic acid sequence in two or more collections of nucleic acid molecules. The method comprises (a) providing a microarray having polynucleotides comprising determinable nucleic acid; (b) contacting the array with (i) a first collection of labelled nucleic acid comprising a sequence substantially complementary to a nucleic acid of the array, and (ii) at least a second collection of labelled nucleic acid comprising a sequence substantially complementary to a nucleic acid of the array, wherein the first and second labels are distinguishable from each other; and (c) detecting hybridization of the first and second labelled complementary nucleic acids to nucleic acids of the arrays.

Electrochemical detection of DNA fragments using a electroconductive microarray having an array of electrodes on which probe molecules of DNA fragment is disclosed in U.S. Pat. Nos. 4,840,893 and 5,776,672.

P. E. Nielsen et al., Science, 254, 1497–1500(1991) and P. E. Nielsen et al., Biochemistry, 36, pp. 5072–5077 (1997) describe PNA (Peptide Nucleic Acid or Polyamide Nucleic Acid) which has no negative charge and functions in the same manner as DNA does. PNA has a polyamide skeleton of N-(2-aminoethyl)glycine units and has neither glucose units nor phosphate groups.

Since PNA is electrically neutral and is not charged in the absence of an electrolytic salt, PNA is able to hybridize with a complementary nucleic acid to form a hybrid structure which is more stable than hybrid given by a DNA prove and its complementary nucleic acid (Pre-print of the 74th Spring Conference of Japan Chemical Society, pp. 1287, reported by Naomi Sugimoto).

The aforementioned P. E. Nielsen et al., Science, 254, 1497–1500(1991) also describes a PNA probe labelled with isotope element and a detection method of a complementary nucleic acid.

SUMMARY OF THE INVENTION

It is an object of the present invention to provide a method of detecting nucleic acid fragments in two or more samples which are supposed to contain the same DNA fragments but contain certain different DNA fragments. The detected data are compared with each other to detect the difference of DNA fragment composition between these samples.

It is a specific object of the invention to provide a method of detecting nucleic acid fragments for analysis of gene expression.

It is another specific object of the invention to provide a method of detecting nucleic acid fragments in plural samples obtained from origins relating to each other, for instance, obtained from normal cells and abnormal cells, or wild strains and their mutants.

The present invention resides in a method of detecting nucleic acid fragments in plural samples which comprises the steps of:

attaching an electroconductive label to nucleic acid fragments in one sample and attaching another electroconductive label to nucleic acid fragments in another sample, the former electroconductive label and the latter electroconductive label having oxidation-reduction potentials differing from each other;

preparing a mixture of the samples containing nucleic acid fragments to which electroconductive labels are attached;

bringing the mixture into contact with an electroconductive microarray having plural electrodes onto which probe molecules complementary to the nucleic acid fragments are fixed, so that hybridization between the nucleic acid fragments having electroconductive labels and the probe molecules on the electroconductive microarray can proceed to form hybrid structures on the electrodes;

applying to the electrode an electric potential corresponding to the oxidation-reduction potential of the former electroconductive label and detecting on the electrode an electric current flowing along the hybrid structure;

applying to the electrode an electric potential corresponding to the oxidation-reduction potential of the latter electroconductive label and detecting on the electrode an electric current flowing along the hybrid structure;

and comparing the electric current detected in the former detecting procedure and the electric current detected in the latter detecting procedure.

The probe molecules are preferably DNA fragments or PNA fragments.

DETAILED DESCRIPTION OF THE INVENTION

[Procedures of Detection Method]

Figure 1:
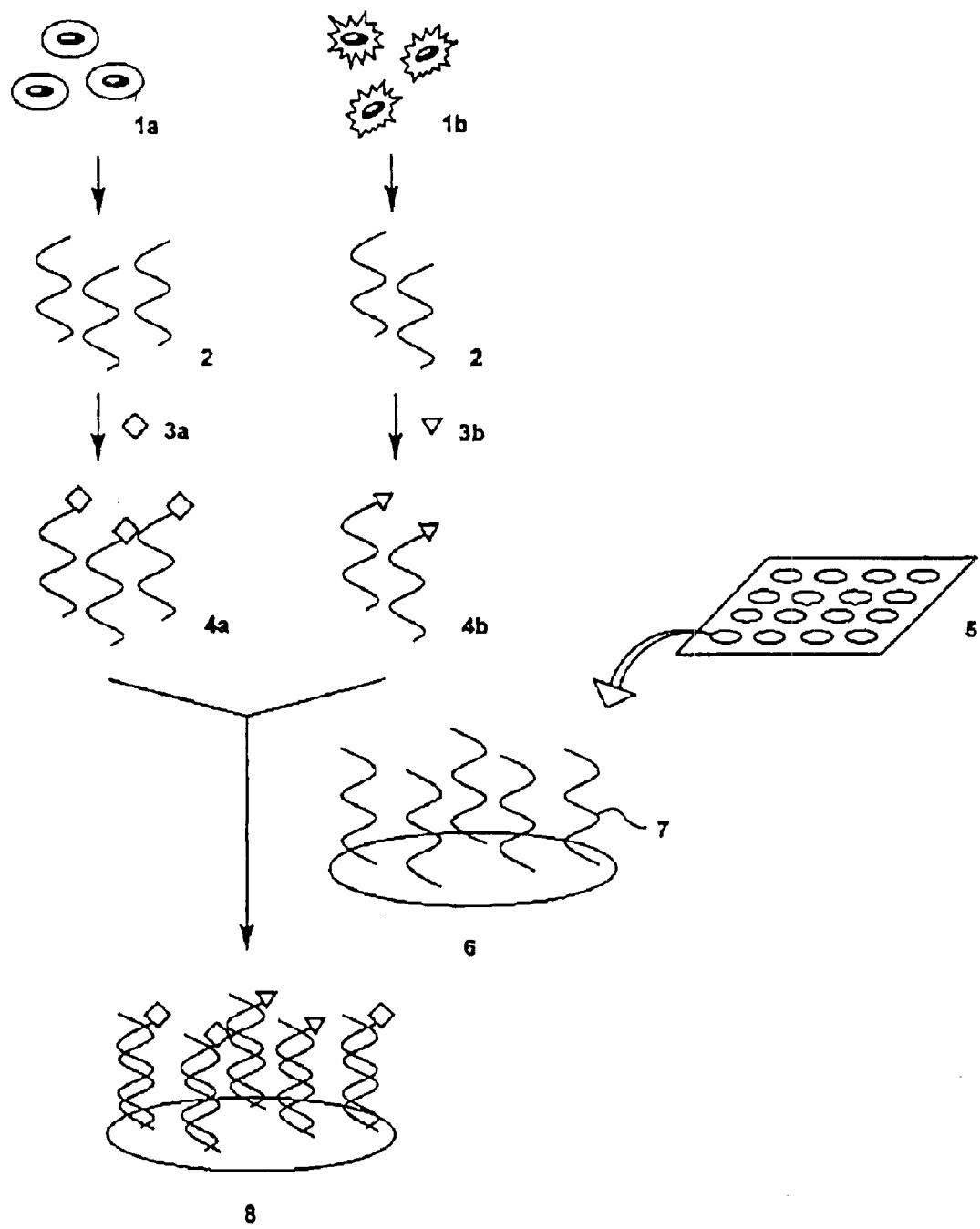
FIG. 1 schematically shows representative procedures of the method of detecting nucleic acid fragments according to the invention.

The method of detecting nucleic acid fragments is explained by referring to the procedures illustrated in FIG. 1.

The sample 1a and sample 1b contain the same DNA fragments 2 in different amounts. To the DNA fragments 2 in the sample 1a and sample 1b are attached, respectively, an electroconductive label 3a and another electroconductive label 3b. Thus, a sample containing electroconductive label-attached DNA fragments 4a and a sample containing electroconductive label-attached DNA fragments 4b are separately produced. The samples are then mixed to give a mixture containing the electroconductive label-attached DNA fragments 4a as well as the electroconductive label-attached DNA fragments 4b.

The mixture is spotted on an electroconductive microarray 5 having plural electrodes 6 on which probe molecules 7 are fixed, so that hybridization takes place to produce hybrid structures 8 on the electrodes.

The hybrid structures 8 can be detected by measuring an electric current on the electrode 6 which flows along the line connecting the electrode 6 and electroconductive label 3a or 3b, when an electric potential corresponding to the oxidation-reduction potential of the electroconductive label 3a or 3b is applied on the electrode. When an electric potential corresponding to the oxidation-reduction potential of the electroconductive label 3a is applied to the electrode, an electric current corresponding to the amount of the hybrid structure containing the label 3a is detected. When an electric potential corresponding to the oxidation-reduction potential of the electroconductive label 3b is applied to the electrode, an electric current corresponding to the amount of the hybrid structure containing the label 3b is detected.

Comparison of the electric current teaches a ratio of content of DNA fragments 2 between sample 1a and sample 1b. The oxidation-reduction potential of the electroconductive label means a value (in terms of voltage) of electric potential at which the maximum electric current is produced.

The samples 1a, 1b preferably contain at least certain number of the same DNA fragments. Some DNA fragments in both samples may be different from each other. Even in the nucleic acid fragment detection using three or more samples, the samples preferably contain at least certain number of the same DNA fragments, while some DNA fragments in the plural samples may be different from each other.

[Detection Tool—Electroconductive Microarray]

The electroconductive microarray having plural electrodes on which probe molecules such as DNA fragments are fixed is known as a tool for fixing complementary nucleic acid fragments to the probe molecules by hybridization. This tool can be called "Electroconductive DNA Chip".

[Electrode]

The electroconductive substrate (e.g., electrode) may be provided on an electro-insulating support material. The electrode and the support material preferably have a weak hydrophilic surface or a hydrophobic surface. The electroconductive substrate may have a plain surface or a surface having many fine concaves and convexes.

The electro-insulating support material can be prepared from glass, ceramics, polymer materials (e.g., polyethylene terephthalate, cellulose acetate, polycarbonate of Bisphenol A, polystyrene, poly(methyl methacrylate), silicon, active carbon, and porous materials (e.g., porous glass, porous ceramics, porous silicon, porous active carbon, cloth, knitted cloth, non-woven cloth, filter paper, and membrane filter). Polymer materials, glass, and silicon are preferably employed.

Generally, the electro-insulating support material is employed in the form of a sheet (or film). The sheet of the support material preferably has a thickness in the range of 100 to 1,000 $\mu$m.

The electroconductive substrate can be made of electrode material, optical fiber, photodiode, thermistor, piezo electrical element, or surface elasticity element. The electrode material is generally employed. The electrode can be carbon electrode of graphite or glassy carbon noble metal electrode of platinum, gold, palladium, or rhodium, metal oxide electrode of titanium dioxide, tin oxide, manganese oxide, or lead oxide, semiconductor electrode of Si, Ge, ZnO, or Cds, or electron conductor of titanium. Preferred are glassy carbon electrode and gold electrode. The electrode may be covered with electroconductive polymer film or monomolecular film.

The electroconductive DNA chip of the invention is preferably composed of a hydrophobic, electro-insulating support material, a plurality of hydrophobic electroconductive substrates placed on the support material, a plurality of DNA fragments fixed on each of the electroconductive substrates. Each of the electrodes is preferably arranged apart from the adjoining electrodes so that each electrode is insulated from the adjoining electrodes. The electrodes may be placed on the support material via an intermediate layer such as a hydrophilic intermediate layer which may have electron charges.

An example of the structure composed of an electro-insulating support material and a plurality of electrodes arranged on the support material is a silicon chip described in Sosnowski, R. G., et al., Proc. Natl. Acad. USA, 94, 1119–1123(1997). The electrodes may be produced on a polymer film using a composite sheet of a polymer film and a metal film.

[Probe Molecules]

The probe molecules to be fixed onto the electrode are nucleic acid fragments (such as DNA fragments, synthesized oligonucleotides, and peptide nucleic acid fragments). The nucleic acid fragment to be fixed onto the electrode preferably is one of 3 to 50 mers, more preferably 10 to 25 mers.

If the electroconductive DNA chip comprises plural DNA chip units each of which has an electrode and probe molecules fixed onto the electrode, the plural electro-chemical DNA chip units can have the same probe molecules or different probe molecules.

Fixation of the probe molecules onto the electrode can be done by any of known methods. For instance, DNA fragments having a reactive group on one end can be fixed onto the electrode through covalent bond by the reaction of the reactive group and the functional group of the surface of the electrode. For instance, a mercapto group is attached to DNA fragment at its 5'- or 3'-terminal, and the mercapto group is then caused to react with a gold electrode, so that an electrode having DNA fragments fixed thereon is produced. The procedure for attaching a mercapto group to DNA fragments is described in M. Maeda, et al., Chem. Lett., 1805–1808(1994) and B. A. Connolly, Nucleic Acids Res., 13, 4484(1985).

If the electrode is made of glassy carbon, the glassy carbon electrode is oxidized by potassium permanganate to produce a carboxylic acid group on the electrode. The carboxylic acid group on the electrode forms an amide bonding with DNA fragment so that the DNA fragment is fixed onto the substrate. See K. M. Millan, et al., Analytical Chemistry, 65, 2317–2323(1993).

Probe molecules such as DNA fragments may be fixed to the electrode, initially, in the form of hybrid DNA fragments. For instance, the hybrid DNA fragments are combined with a mercapto group at their 5'- or 3'-terminals (preferably 5'-terminals) of their single fragments, and are brought into contact with a gold electrode, so that the hybrid DNA fragments are fixed on the electrode. The hybrid DNA fragment fixed on the electrode is then processed to dissociate a single fragment having no mercapto group, so that the desired electroconductive DNA chip is produced.

The covalent bond between the DNA fragment and the electrode can be formed using an amino group, an aldehyde group, a mercapto group, or a biotin molecule which is attached to the DNA fragment.

The probe molecules such as DNA fragments having a reactive group on one end can be fixed onto an electrode by spotting onto the electrode an aqueous solution containing the DNA fragments. The aqueous solution preferably contains the DNA fragments in a concentration of several pM to several mM. The volume for the spotting generally is in the range of 1 to 100 nL, preferably 1 to 10 nL. The aqueous solution may contain a viscosity increasing additive such as sucrose, polyethylene glycol, or glycerol. The spotting can be made manually or utilizing a commercially available spotter. The spotted solution is then kept on the electrode at a predetermined temperature for several hours (namely, incubation), whereby the DNA fragments are fixed onto the electrode by covalent bonding. After the incubation is complete, free DNA fragments (which are not fixed onto the electrode) are preferably washed out.

The DNA fragments are preferably fixed onto the electrode in an amount of $10^{-20}$ to $10^{-12}$ mol./mm$^2$ of the surface area of the electrode. The amount of the fixed DNA fragments can be determined by means of HPLC (high performance liquid chromatography) or other analytical apparatuses.

Otherwise, probe molecules can be synthesized on the substrate by a known method.

[Peptide Nucleic Acid —PNA]

The PNA preferably employable in the invention has the following formula:

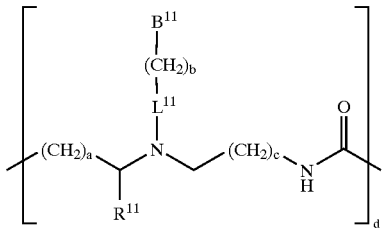

In the formula, the symbols of $B^{11}$, $R^{11}$, $L^{11}$, a, b, c, and d have the meanings described below.

$B^{11}$ is a ligand and represents one of bases of natural nucleic acids (i.e., A, T, C, G, I, or U) or its analogue. $B^{11}$ is bonded through the 9th position in the case that the base is a purine base such as adenine, guanine or inosine, and through the 1st position in the case that the base is a pyrimidine base such as thymine, uracil or cytosine. The base analogue is an organic base which is similar to the base of natural origin in its chemical structure, for instance, a base group which is prepared by replacing the carbon or nitrogen atom of the purine or pyrimidine ring with a nitrogen or carbon atom, respectively, or a base group modifying the purine or pyrimidine ring with a substituent such as a sulfhydryl group or a halogen atom. Otherwise, $B^{11}$ can be an aromatic moiety containing no nucleic acid base, an alkanoyl group having 1 to 4 carbon atoms, a hydroxyl group, or a hydrogen atom. Examples of the base analogues include 7-deazaadenine, 6-azauracil, and 5-azacytosine. $B^{11}$ also can be a reporter ligand, a protein label such as hapten or biotin, a spin label, or a radioactive label. Particularly preferred are nucleic acid bases (i.e., A, T, C, G, and U).

$R^{11}$ is a hydrogen atom or a group derived from a side-chain of an α-amino acid of natural origin. Examples of such groups include an alkyl group having 1 to 6 carbon atoms, an aryl group having 6 to 20 carbon atoms, an aralkyl group having an alkyl group of 1 to 6 carbon atoms, a heteroaxyl group having 6 to 20 carbon atoms, a hydroxyl group, an alkoxy group having 1 to 6 carbon atoms, an alkylthio group having 1 to 6 carbon atoms, a group of —NR$^{13}$R$^{14}$ [each of R$^{13}$ and R$^{14}$ independently is a hydrogen atom, an alkyl group having 1 to 3 carbon atoms, an alkoxy group having 1 to 3 carbon atoms, an alkylthio group having 1 to 3 carbon atoms, or a hydroxyl group], and a mercapto group. $R^{11}$ may form an alicyclic ring or a heterocyclic ring in combination with the carbon atom to which $R^{11}$ is attached.

$L^{11}$ is a linking group such as a divalent group represented by the group of —CO— or —CONR$^{12}$— [R$^{12}$ is a hydrogen atom, an alkylene group having 1 to 4 carbon atoms, a hydroxyl group, an alkoxy group having 1 to 4 carbon atoms, or an amino group], or an alkylene group having 1 to 4 carbon atoms. The alkoxy group and amino group may have one or more substituents such as alkyl of 1–4 carbon atoms, alkoxy of 1–4 carbon atoms, and hydroxyl.

Each of a, b and c independently is an integer of 0 to 5, preferably 1, and d is an integer of 1 to 60, preferably an integer of 1 to 40.

A particularly preferred PNA fragment has the following formula, in which each of $B^{11}$ and d has the same meaning as described above for the above-illustrated formula:

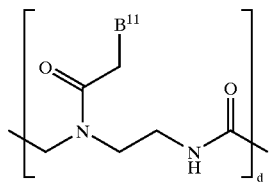

[Target Samples Containing Nucleic Acid Fragments]

The target samples preferably contain cDNA fragments which can be produced by reverse transcription using mRNA present in living organisms or human beings. The mRNA can be collected from samples of different gene expressions. The mRNA may be obtained from origins relating to each other, for instance, obtained from normal cells and abnormal cells, or wild strains and their mutants.

Otherwise, various DNA fragments can be employed.

[Attachment of Electroconductive Label]

The attachment of an electroconductive label to DNA fragments is described in S. Takenaka et al., Analytical Biochemistry, 218, 436–443 (1993).

The electroconductive label-attached DNA fragments also can be prepared by incorporating dNTP having an electroconductive label into the target DNA fragments by reverse transcription.

The electroconductive label having an oxidative-reductive activity can be an organic metal compound or a compound containing no metal atoms.

The organic metal compound preferably is a π-complex in which a surrounding ligand can supply electron to the center metal atom as well as an electron is supplied from the orbit of the metal atom to the vacant orbit of the ligand. A typical example of the π-complex is a metallocene having the following formula:

(A-1)

(A-2)

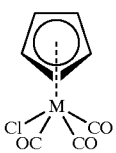
(A-3)

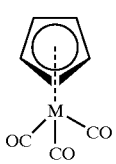
(A-4)

(A-5)

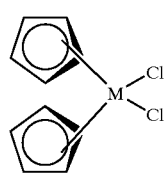
(A-6)

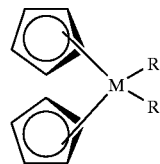
(A-7)

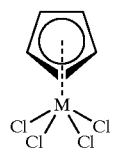
(A-8)

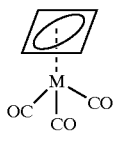
(A-9)

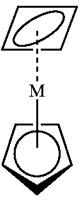
(A-10)

In the above-illustrated formula, the metal atom (M) of the metallocene can be Fe, Ni, Co, Mo, Zn, Cr, Tl, Ta, Ti, Cu, Mn, W, V, Ru or Os. Most preferred is Fe.

Other examples of the π-complexs include cyclobutadienyl complex, cyclopentadienyl complex, phenanthroline complex, bipyridyl complex, and triphenylphosphine complex.

Examples of the phenanthroline complexes include tris(phenanthroline) zinc complex, tris(phenanthroline) ruthenium complex, tris(phenanthroline) cobalt complex, di(phenanthroline) zinc complex, di(phenanthroline) ruthenium complex, di(phenanthroline) cobalt complex, and phenanthroline platinum complex.

Examples of the bipyridyl complexes include bipyridyl platinum complex, tris(bipyridyl) zinc complex, tris(bipyridyl) ruthenium complex, tris(bipyridyl) cobalt complex, di(bipyridyl) zinc complex, di(bipyridyl) ruthenium complex, and di(bipyridyl)cobalt complex.

Examples of the triphosphine complexes include $COCH_3(PPh_3)_3$, $CoH(N_2)(PPh_3)_3$, $RuH_2(PPh_3)_4$, and $RhH(PPh_3)_4$. In the formula, Ph stands for phenyl group.

Other examples of the electroconductive complexes include porphyrins such as chlorophyll, vitamin $B_{12}$, heme, chlorocruoroheme, and chlorophylide.

Examples of the electroconductive compounds having no metal atom include biologen (described hereinbelow) and 2,2'-bipyridine (described hereinbelow), 1,10-phenanthroline, and catecholamine. In the below-described formula, each of $R^A$ and $R^B$ independently represents an alkyl group having 1 to 6 carbon atoms, an alkoxy group having 1 to 6 carbon atoms, an aryl group having 6 to 12 carbon atoms, or a heterocyclic group having 2 to 12 carbon atoms and 1 to 4 hetero atoms such as N, O, and S.

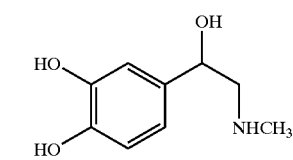
(A-13)

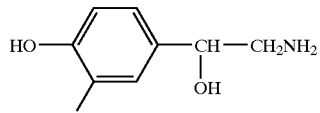
(A-14)

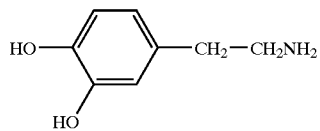
(A-15)

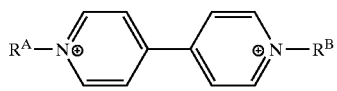
(A-16)

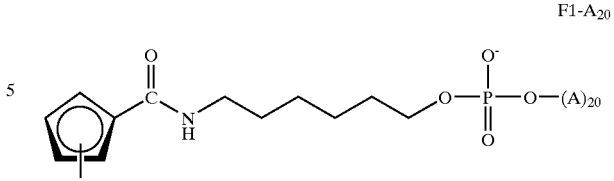
F1-A$_{20}$

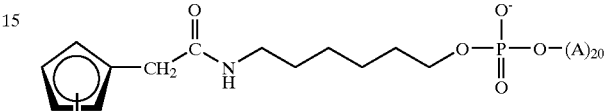
F2-A$_{20}$

[Hybridization]

The hybridization can be performed essentially in the same manner as that employed in various assay procedures utilizing the conventional DNA chip.

The hybridization is preferably performed at a temperature between room temperature and approximately 70° C., for 0.5 to 20 hours.

[Detection of Label on Substrate]

The electroconductive label attached to the substrate by the formation of hybrid structure can be detected by measuring an electric current flowing from the electrode to a counter-electrode (or vice versa) along the hybrid structure. The measurement of electric current can be performed by any of known methods such as cyclic voltamography (CV), differential pulse voltamography (DPD), and potentiostat, preferably in the applied voltage range of 0 to 800 mV. The differential pulse voltamography is most preferred.

The present invention is further described by the following examples.

EXAMPLE 1

(1) Preparation of Electroconductive DNA Chip

On a gold electrode (surface area: 2.25 mm$^2$) was spotted 2 μL of an aqueous solution containing thimine 20 mers having a mercaptohexyl group at its C-terminal (HS-dT$_{20}$, in an amount of 100 pico mol./μL), and the electrode was allowed to stand for one hour at room temperature. The electrode was washed with super pure water to give an electroconductive DNA chip.

(2) Preparation of Sample DNA Fragments

To 20 mers adenines were attached two ferrocene compounds having different oxidation-reduction potentials, in the manner described in Takenaka, et al., Analytical Biochemistry, 218, 436–443 (1994). Thus, two ferrocene-labelled sample DNA fragments F1-A$_{20}$ and F2-A$_{20}$ illustrated below were prepared.

(3) Hybridization on Electroconductive DNA Chip

Two μL of an aqueous solution (10 mM Tris buffer, pH 7.5) containing 80 pico mol./μL of the electroconductive label-attached adenine (F1-A$_{20}$ or F2-A$_{20}$) prepared in (2) above was spotted on the electroconductive DNA chip prepared in (1), and the spotted chip was allowed to stand at 25° C. for 30 min, for incubation. The DNA chip was washed out with pure water, to remove unhybridized electroconductive label-attached adenine.

(4) Measurement of Electric Current

The electroconductive DNA chip on which the electroconductive label-attached adenines were fixed by hybridization was placed in a buffer solution [0.1 M potassium chloride—0.1 M acetic acid buffer, pH 5.6], and differential pulse voltamometry was carried out in the applied voltage range of 100 to 700 mV.

Figure 2:
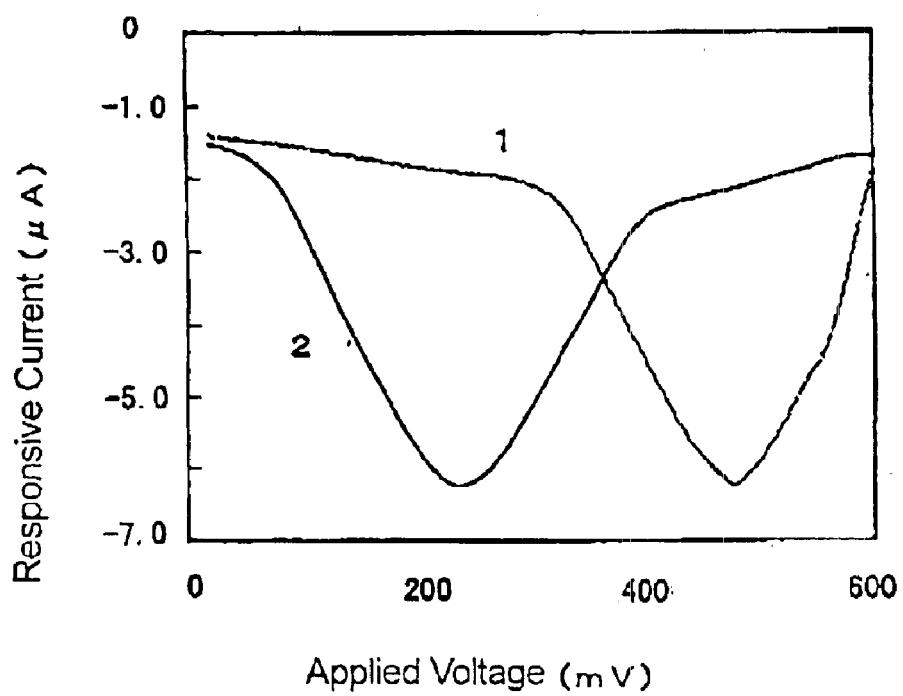
FIG. 2 illustrates a graph obtained in Example 1 in which a relationship between an applied voltage and a responsive electric current is shown.

A responsive electric current of 6.0 μA was detected at 460 mV on the DNA chip on which F1-A$_{20}$ was fixed (FIG. 2, curve-1), while a responsive electric current of 6.0 μA was detected at 260 mV on the DNA chip on which F2-A$_{20}$ was fixed (FIG. 2, curve-2).

EXAMPLE 2

The procedures of Example 1 were repeated except that a buffer solution containing 40 picomol. of F1-A$_{20}$ and 40 picomol. of F2-A$_{20}$ was employed.

The same procedures were repeated except for using a buffer solution containing 80 picomol. of F1-A$_{20}$ only, a buffer solution containing 60 picomol. of F1-A$_{20}$ and 20 picomol. of F2-A$_{20}$ a buffer solution containing 20 picomol. of F1-A$_{20}$ and 60 picomol. of F2-A$_{20}$, and a buffer solution containing 80 picomol. of F2-A$_{20}$ only.

Figure 3:
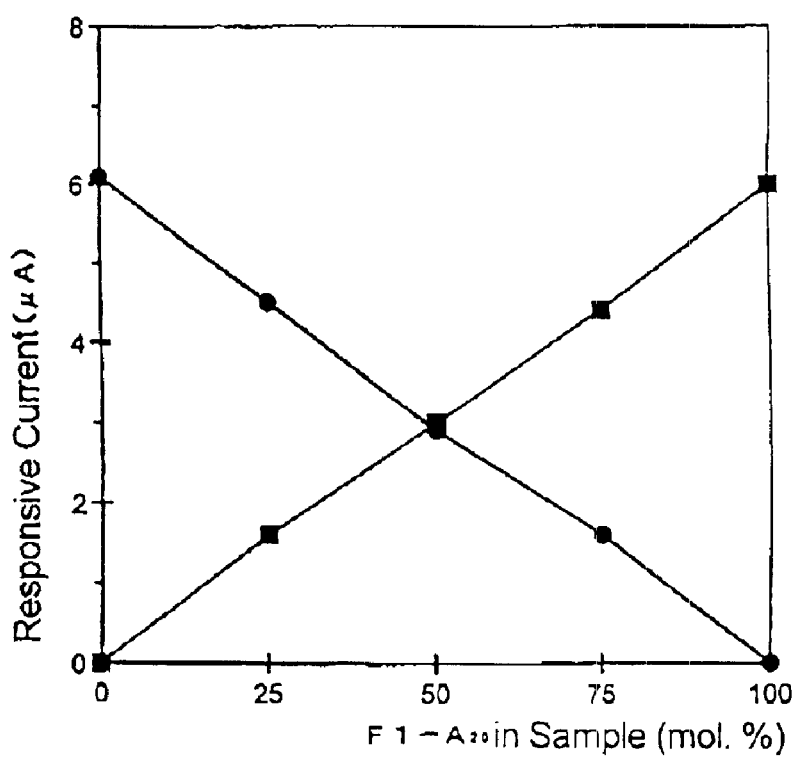
FIG. 3 illustrates a graph obtained in Example 2 in which a relationship between a ratio of $F1-A_{20}$ or $F2-A_{20}$ in the sample mixture and a responsive electric current is shown.

The electric currents produced at 260 mV and 460 mV were then detected in each buffer solution. The results are illustrated in FIG. 3. The strength of peak current linearly varies with the ratio of the concentrations of F1-A$_{20}$ and F2-A$_{20}$.

EXAMPLE 3

(1) Preparation of Peptide Nucleic Acid Fragment

Peptide nucleic acid fragment [PNA-H$_2$N-Lys-T$_{10}$-H, hereinafter referred to as PNA-T$_{10}$] having the below-illustrated formula was prepared in the manner described in P. E. Nielsen, et al., Journal of American Chemical Society, 114, 1895–1897(1992) and ibid., 114, 9677–9678 (1992). In the formula, T stands for thimine, and the left terminal is C-terminal and the right terminal is N-terminal.

PNA-T$_{10}$

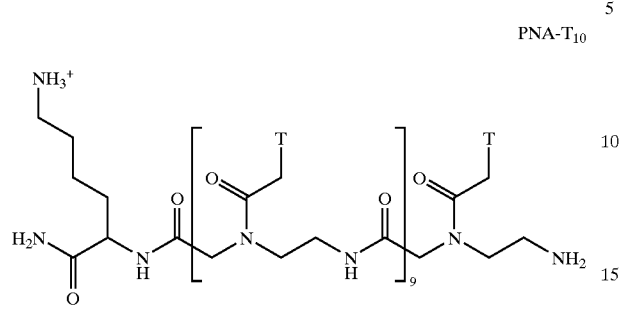

(2) Preparation of Electroconductive PNA Chip

On a gold electrode (surface area: 2.25 mm$^2$) having mercapto groups on its surface was spotted an aqueous phosphate buffer containing 1,2-bis(vinylsulfonylacetamide)ethane so that a gold electrode having reactive vinylsulfonyl groups on its surface were prepared. On thus prepared reactive electrode was spotted 2 μL of an aqueous solution containing PNA-T$_{10}$, and the electrode was allowed to stand for one hour at room temperature. The electrode was washed with super pure water to give an electroconductive PNA chip.

(3) Preparation of Sample PNA Fragments, Hybridization on Electroconductive PNA Chip, and Measurement of Electric Current The procedures of Example 2 were repeated.

(4) Results of Measurement of Electric Current

Figure 4:
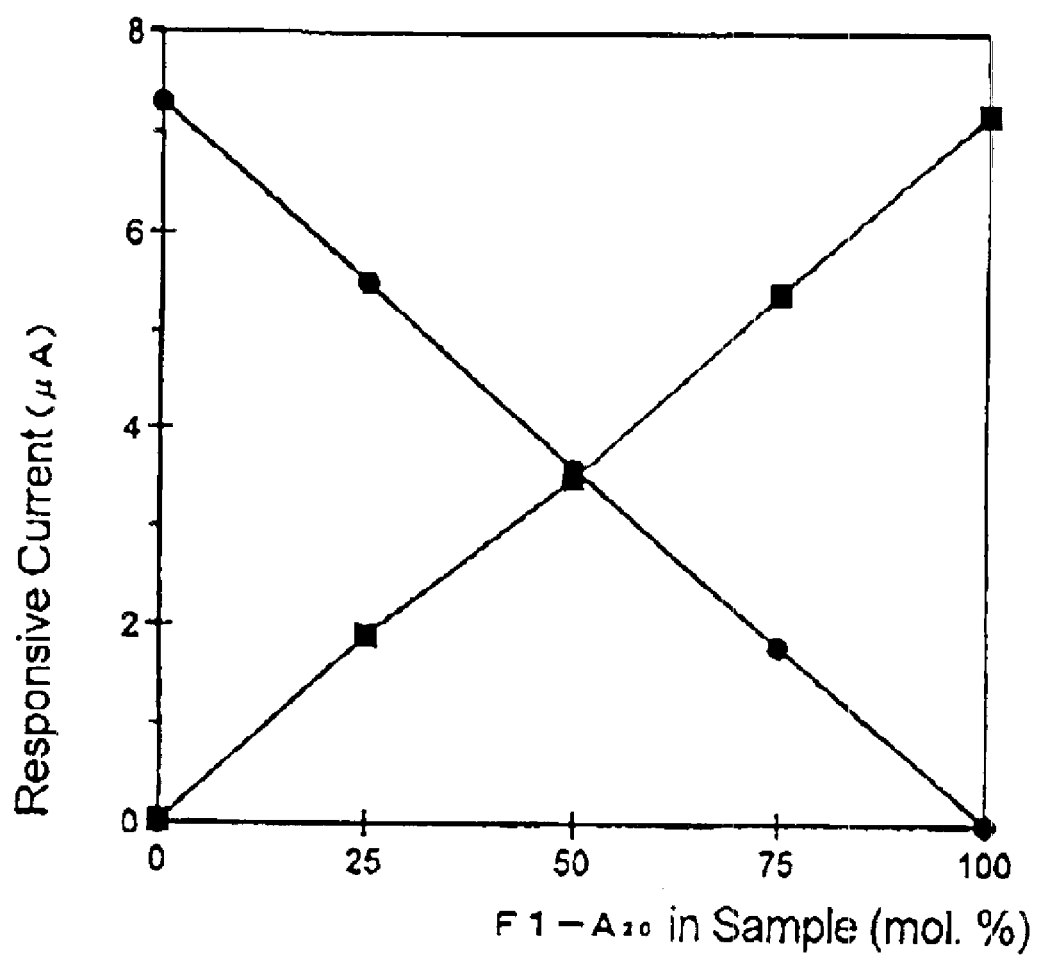
FIG. 4 illustrates a graph obtained in Example 3 in which a relationship between a ratio of $F1-A_{20}$ or $F2-A_{20}$ in the sample mixture and a responsive electric current is shown.

The results are illustrated in FIG. 4. The strength of peak current linearly varies with the ratio of the concentrations of F1-A$_{20}$ and F2-A$_{20}$. It is noted that the sensitivity is higher than that observed in Example 1 using an electroconductive DNA chip.

What is claimed is:

1. A method of detecting a ratio of content of complementary nucleic acid fragments contained in plural samples which comprises the steps of:

attaching an electroconductive label to nucleic acid fragments in one sample and attaching another electroconductive label to nucleic acid fragments in another sample, the former electroconductive label and the latter electroconductive label having oxidation-reduction potentials differing from each other;

preparing a mixture of the samples containing nucleic acid fragments to which electroconductive labels are attached;

bringing the mixture into contact with an electroconductive microarray having plural electrodes onto which probe molecules complementary to the nucleic acid fragments are fixed, so that hybridization between the nucleic acid fragments having electroconductive labels and the probe molecules on the electroconductive microarray can proceed to form hybrid structures on the electrodes;

applying to the electrode an electric potential corresponding to the oxidation-reduction potential of the former electroconductive label and detecting on the electrode an electric current flowing along the hybrid structure;

applying to the electrode an electric potential corresponding to the oxidation-reduction potential of the latter electroconductive label and detecting on the electrode an electric current flowing along the hybrid structure; and comparing the electric current detected in the former detecting procedure and the electric current detected in the latter detecting procedure, whereby detecting the ratio of content of the complementary nucleic acid fragments between plural samples.

2. The method of claim 1, wherein the probe molecules are nucleic acid fragments.

3. The method of claim 1, wherein the probe molecules are peptide nucleic acid fragments.

4. The method of claim 1, wherein the oxidation reduction potential of the latter electroconductive label differs from the oxidation-reduction potential of the former electroconductive label by at least 50 mV.

5. The method of claim 4, wherein the oxidation reduction potential of the former electroconductive label and the oxidation-reduction potential of the latter electroconductive label both are in the range of 0 to 800 mV.

6. The method of claim 1, wherein the detections of electric current on the electrode are conducted by differential pulse voltamography.

7. The method of claim 1, wherein one sample is obtained from normal cells and another sample is obtained from abnormal cells corresponding to the normal cells.

8. The method of claim 1, wherein one sample is obtained from wild strain and another sample is mutant thereof.

* * * * *